United States Patent [19]

Malone

[11] 4,172,092

[45] Oct. 23, 1979

[54] PRODUCTION OF THIOCARBOHYDRAZIDE

[75] Inventor: James R. Malone, Dormagen, Fed. Rep. of Germany

[73] Assignee: Mobay Chemical Corporation, Pittsburgh, Pa.

[21] Appl. No.: 641,705

[22] Filed: Dec. 17, 1975

[51] Int. Cl.² .......................................... C07C 159/00
[52] U.S. Cl. ................................................ 260/552 SC
[58] Field of Search .................................. 260/552 SC

[56] References Cited

U.S. PATENT DOCUMENTS

| | | | |
|---|---|---|---|
| 2,726,263 | 12/1955 | Audrieth et al. | 260/552 SC |
| 3,929,877 | 12/1975 | Toth et al. | 260/552 SC |
| 4,132,736 | 1/1979 | Cramm et al. | 260/552 SC |

*Primary Examiner*—Thomas Waltz
*Attorney, Agent, or Firm*—Sprung, Felfe, Horn, Lynch & Kramer

[57] ABSTRACT

In the production of thiocarbohydrazide wherein hydrazine is reacted with carbon disulfide in the presence of water and the reaction product is thereafter heated to evolve hydrogen sulfide, the improvement which comprises effecting the reaction with carbon disulfide in the presence of hydrogen sulfide, whereby the yield of thiocarbohydrazide is increased. At the end of the reaction, the thiocarbohydrazide is filtered off and the mother liquor, after a portion is concentrated and still containing hydrogen sulfide as well as excess hydrazine, is recycled to the next cycle as the source of hydrogen sulfide.

11 Claims, No Drawings

PRODUCTION OF THIOCARBOHYDRAZIDE

This application relates to the production of thiocarbohydrazide from hydrazine and carbon disulfide.

Already several processes for the manufacturing of thiocarbohydrazide are known (F. Kurzer and M. Wilkinson, Chem. Rev. 113 (1969). This compound is obtained during the hydrazinolysis of thiophosgene in moderate yields. Hereby ether (Stolle et al., Ber. 41, 1099 (1908)) or water (Authenrith and Hefner, Ber. 58, 2151 (1925)) can be used as reaction media. It is further known how to manufacture this compound through hydrazinolysis of diethylxanthate (Guha et al., J. Chem. Soc. 125, 1215 (1924)). By merely heating the two reaction components in the absence of a solvent yields of 70-74% of theory are obtained (Beyer et al., Ber. 87, 1401 (1954)). It is also known to prepare thiocarbohydrazide through conversion of dialkyltrithiocarbonates with hydrazine (Sandstroem, Arkiv Kemi 4, 297 (1952)). Also cyclic trithiocarbonate can be used for this synthesis, e.g., ethylenetrithiocarbonate gives pure thiocarbohydrazide in a yield of 71% of theory. The hydrazinolysis of methyl-dithiocarbazinate leads to a yield of 65% of theory of thiocarbohydrazide (Audrieth et al., J. Org. Chem. 19, 733 (1954)).

The most common and cheapest synthesis of the thiocarbohydrazide is, however, the conversion of carbon disulfide with hydrazine. Here at first hydrazinium-dithiocarbazinate forms according to equation (1):

$$CS_2 + 2H_2NNH_2 \rightarrow H_2NNHCSSH.NH_2NH_2 \qquad (1)$$

This compound is converted to thiocarbohydrazide with evolution of hydrogen sulfide according to equation (2):

$$H_2NNHCSSH.NH_2NH_2 \rightarrow H_2NNHCSNHNH_2 + H_2S \qquad (2)$$

Better yields and purer product are obtained when the hot aqueous solution of the hydrazinium-dithiocarbazinate is digested with lead oxide (Stolle, et al., Ber. 41, 1099 (1908)).

The yields of thiocarbohydrazide can also be increased when conducting the decomposition of hydrazinium-dithiocarbazinate in aqueous solution in the presence of hydrazine (Audrieth et al., J. Org. Chem. 19, 733 (1954); U.S. Pat. No. 2,726,263). It was found that with increasing dilution of the hydrazine containing reaction medium with water the yield of TCH decreases. The use of a waterfree solvent for hydrazine, e.g., methyl, ethyl, or propyl alcohol, however, does not increase the TCH yield. To conduct this common process the hydrazinium-dithiocarbazinate which is obtained in the usual way through conversion of carbon disulfide with hydrazine hydrate, is heated in an aqueous hydrazine solution at approximately 95° C. for 1-2 hours under reflux. For each mole of hydrazinium-dithiocarbazinate, 1 to 3 moles of hydrazine are used. According to another variation of this known process carbon disulfide is treated while cooling in aqueous solution with 3 to 6 times the amount of hydrazine and is then heated. In both processes the yield can be increased by repeatedly removing the TCH from the reaction mixture which forms during the course of the conversion. However, also with this method the yield is only 53.3% of theory. It is further known to convert the hydrazinium-dithiocarbazinate thermally, obtained in the usual way to TCH. Hereby yields of approximately 70% of theory are obtained (Petri, Z. Naturforsch. 16 B, 769 (1961)).

It is an object of this invention to produce thiocarbohydrazide economically in high yield.

This object is realized in accordance with the present invention pursuant to which thiocarbohydrazide is produced by reacting carbon disulfide with hydrazine in the presence of water and hydrogen sulfide and thereafter heating. Thiocarbohydrazide is recovered as a solid from the mother liquor which, optionally after a portion is concentrated, is recycled for further reaction, constituting a source of water and hydrogen sulfide. Desirably the hydrazine is present in about 2 to 5 times the molar amount of the carbon disulfide, excess hydrazine also being recycled in the mother liquor.

The reaction between carbon disulfide and hydrazine can be effected at a temperature up to about 45° C., e.g., about 30° to 45° C., or even slightly higher although it may be as low 0° C.

Temperatures below room temperature may result in precipitation of intermediate solids which make the vessel contents difficult to agitate, especially on a large scale. Higher temperatures avoid this problem but, if temperatures approaching 45° C. or even higher are employed, special measures should be taken to ensure that the carbon disulfide reacts fully rather than rapidly evaporating and entering the gas space above the reaction solution. To this end, the carbon disulfide may be introduced under pressure below the level of the solution with measures taken to ensure its complete reaction, e.g., strong agitation and/or use of a nozzle which produces fine jets of widely dispersed carbon disulfide with much surface area for quick reaction.

The hydrazine is usually present in excess of the stoichiometric amount which is twice the molar amount of the carbon disulfide. About 2 to 5 times the molar amount is usually employed, preferably at least about 2.2 times the molar amount. Hydrazine may be added as such or in the form of hydrazine hydrate or as an aqueous solution, taking into account the amount of water carried therewith, if any. When mother liquor is recycled, the amount of hydrazine contained therein may be taken into consideration when calculating the amount of hydrazine needed for the next cycle.

The amount of water present during the reaction may be varied widely, e.g., about 0.5 to 3 and preferably about 1 to 2 times as much water by weight as hydrazine hydrate. If desired, relatively small amounts of water per se or as mother liquor may be present during the reaction with carbon disulfide and more added prior to or during the heating.

The heating can be effected up to about 90° C. or even higher, although preferably the temperature is lower, e.g., at least about 50° C. and preferably about 60° to 85° C., especially about 69° to 75° C. The duration will be several hours, the exact time being selected to achieve the best overall yield.

Following heating the reaction mixture is cooled, solid thiocarbohydrazide is separated off as by filtration and is washed. Advantageously the mother liquor is divided and one portion is concentrated, preferably under vacuum, certain components being lost thereby, particularly volatile materials. Another portion still rich in materials from the reaction, including hydrogen sulfide, is combined with the concentrated portion and the combination supplied to the next cycle to supply the water requirement. If desired, some concentration can even be effected during the heating by employing vacuum.

The process produces relatively high yields compared with the prior art. The hydrogen sulfide for the reaction may constitute the product from an earlier cycle wherein hydrogen sulfide was not initially present and, excluding such preliminary cycles, yields of 80% can be achieved.

The invention will be further described in the following illustrative examples wherein all parts are by weight unless otherwise expressed.

EXAMPLE 1

580 ml of 85% hydrazine hydrate (10 moles hydrazine, balance water) are placed in a 3 liter 3-neck flask equipped with thermometer, efficient agitator, dropping funnel, and reflux condenser connected to a caustic trap. The temperature is lowered to 10° C. and 2 moles of carbon disulfide (152 grams, 121 ml) are dropped in while maintaining the temperature below 15° C. 1500 ml of mother liquor from a previous cycle are added and the temperature is raised to 85° C. and held there for 1.5 hours. The temperature is then lowered to 10° C., the product filtered and washed with water. 163 grams of thiocarbohydrazide (TCH) are recovered, i.e., 77% yield based in carbon disulfide.

EXAMPLE 2

The process of Example 1 is repeated with the following exceptions: The amount of carbon disulfide is doubled and immediately after the temperature reaches 85° C. it is allowed to drop to 60° C. With recycling the yield rises from Cycle 1 (no recycle; water in place of recycled mother liquor) to Cycle 3 as follows:

Table 1

| Cycle | Mother Liquor at end, ml | TCH obtained grams | yield based on $CS_2$, % |
|---|---|---|---|
| 1 | 2028 | 85.8 | 40.5 |
| 2 | 2013 | 108 | 51.0 |
| 3 | 1850 | 189 | 89.2 |

EXAMPLE 3

580 ml of 85% hydrazine hydrate (10 moles) are placed in a 3 liter 3-neck flask equipped with thermometer, efficient agitator, dropping funnel and reflux condenser connected to a caustic trap. The temperature is lowered to 10° C. and the system is placed under $N_2$. 121 ml of $CS_2$ (2 moles) are dropped in while maintaining the temperature below 15° C. 1,500 ml of $H_2O$ are added and the temperature is raised to 85° C. then allowed to cool until gas evolution ceases. The final temperature is 50°-60° C. and is reached after 1-1.5 hours. The temperature is then lowered to 10° C., the product filtered and washed with water. Recycles are run in the same manner except that 1,500 ml of mother liquor are substituted for the 1,500 ml of fresh water.

The results obtained are as follows:

Table 2

| Cycle | Mother Liquor at end, ml | TCH obtained grams | % yield based on $CS_2$ |
|---|---|---|---|
| 1 | 1960 | 97.3 | 45.9 |
| 2 | 1808 | 118 | 55.6 |
| 3 | 1770 | 129.6 | 61.1 |
| 4 | 1234 | 140.5 | 66.0 |
| 5 | 1695 | 137.2 | 64.8 |
| 6 | 1650* | | |
| 7 | 1650 | 155.3 | 73.4 |
| 8 | 1690 | 147.3 | 69.6 |

*Estimated

EXAMPLE 4

177 g of 85% hydrazine hydrate (3 moles) and 93 ml of water are placed in a 500 ml 3-neck flask equipped with thermometer, efficient stirrer, dropping funnel and condenser attached to a caustic trap. 76 ml of carbon disulfide (1.25 moles) are added at 25°-30° C. The mixture is stirred for 1 hour at 30° C. after addition. The reaction mixture is then heated to 60° C. and held for 15 hours while blowing with a mild stream of nitrogen. The mixture is cooled to 15° C., filtered, washed twice with 60 ml of $H_2O$ and dried.

Recycles are runs as above except that the mother liquor from the preceding reaction is concentrated to 93 ml and charged instead of water.

The following results are obtained:

Table 3

| Cycle | TCH obtained grams | % yield based on $CS_2$ | % yield based on $N_2H_4$ |
|---|---|---|---|
| 1 | 81.6 | 61.6 | 51.4 |
| 2[a] | 89.3 | 67.4 | 56.1 |
| 3[b,c] | 108.2 | 81.9 | 68.2 |

[a] 20 hour cook
[b] 13 hour cook
[c] left standing 60 hours before work up after completion of reaction.

EXAMPLE 5

The process of Example 4 is repeated except that 150 g of 85% hydrazine hydrate (2.55 moles) are charged. The reaction mixture kept under nitrogen at all times and the mother liquor concentrated under vacuum after completion of the reaction.

The results obtained are as follows:

Table 4

| Cycle | TCH obtained grams | % yield based on $CS_2$ | % yield based on $N_2H_4$ |
|---|---|---|---|
| 1[a] | 99.1 | 74.9 | 73.5 |
| 2 | 96.1 | 72.5 | 71.3 |
| 3 | 106.6 | 80.5 | 79.0 |
| 4[b] | 93.7 | 70.7 | 69.5 |

[a] 18 hour cook, mother liquor from Example 1 used
[b] Left standing 60 hours after addition of $CS_2$.

EXAMPLE 6

(a) 375 g of 100% hydrazine hydrate (7.5 moles) and 450 g of water are added to a 2 liter 3-neck flask equipped with a thermometer, an agitator and a diptube; through the dip-tube, carrying a spray nozzle at its end, 180 ml of $CS_2$ (3 moles) are injected by a pressure pump under a pressure of 3-4 atmospheres under the surface of the reaction mixture; the temperature is kept between 40°-42° C. by cooling.

After the addition of the $CS_2$ the suspension is heated up to 62°-64° C. and kept at this temperature for 16 hours; after that period the reaction mixture is cooled to 20° C., the crystalline product is removed by filtration and the product is washed 3 times with 100 ml of water.

Yield: 220 g (69% based upon $CS_2$, 56% based upon hydrazine hydrate).

The mother liquor is collected and used in another cycle in place of the dilution water in the following manner: Into 450 ml of mother liquor and 380 g of 100% hydrazine hydrate (7.6 moles) there are charged 210 ml (3.5 moles) of $CS_2$, as described above, at a temperature below 43° C.; after completion of the addition of $CS_2$ the reaction mixture is treated to 62°-64° C. The reaction mixture is kept at this temperature for 10 hours; after this period the reaction mixture is worked up as above.

The results obtained in this and later cycles are as follows:

Table 5

| Cycle | TCH obtained grams | % yields based on $CS_2$ | % yields based on $N_2H_4$ |
| --- | --- | --- | --- |
| 1 | 334 | 90 | 82.7 |
| 2 | 327 | 88.2 | 81.2 |
| 3 | 335 | 90.3 | 82.8 |
| 4 | 322 | 86.8 | 79.8 |
| 5 | 340 | 89.4 | 82.4 |
| Average | 332 | 89.4 | 82.4 |

(b) The excess mother liquor from each cycle, approximately 150 ml per cycle, together with the first wash water of each batch is collected and heated 3 hours at 75° C. The reaction mixture is cooled to 10° C. and the precipitated TCH is isolated by filtration.

On the average this procedure allows recovery of an additional 16.0 g of TCH per cycle. The total yield amounts therefore to 348 g = 93.8% based upon $CS_2$ or 86.5% based on hydrazine.

(c) As an alternative, 400 ml of the total mother liquor of 600 mls from a cycle are concentrated unter reduced pressure at 50°-55° C. to a total of 250 ml; this portion is then added to the untreated 200 ml of mother liquor to make up the 450 ml of aqueous solution required for the next cycle.

Yields for a reaction sequence using this alternative are summarized in Table 6.

Table 6

| Cycle | TCH obtained grams | % yield based on $CS_2$ | % yield based on $H_2N_4$ |
| --- | --- | --- | --- |
| 1 | 345 | 92.7 | 85.6 |
| 2 | 352 | 95.0 | 87.4 |
| 3 | 340 | 91.4 | 85.6 |
| 4 | 340 | 91.4 | 85.6 |
| 5 | 360 | 97.0 | 89.4 |
| Average | 347 | 93.4 | 86.0 |

It will be appreciated that the instant specification and examples are set forth by way of illustration and not limitation, and that various modifications and changes may be made without departing from the spirit and scope of the present invention.

What is claimed is:

1. In the production of thiocarbohydrazide wherein hydrazine is reacted with carbon disulfide in the presence of water and the reaction product is thereafter heated to evolve hydrogen sulfide, the improvement which comprises effecting the reaction with carbon disulfide in the presence of hydrogen sulfide present from the outset, whereby the yield of thiocarbohydrazide is increased.

2. The process of claim 1, wherein the reaction solution is filtered to separate solid thiocarbohydrazide from mother liquor and the water- and hydrogen sulfide-containing mother liquor is recycled to another reaction of carbon disulfide with hydrazine.

3. The process of claim 2, wherein the hydrazine is employed in about 2 to 5 times the molar amount of the carbon disulfide, excess hydrazine being recycled in the mother liquor.

4. The process of claim 2, wherein part of the mother liquor is concentrated prior to recycle.

5. The process of claim 2, wherein the reaction with carbon disulfide is effected at a temperature up to about 45° C. and the heating is effected at a temperature between about 50° C. and the boiling point.

6. The process of claim 4, wherein the hydrazine is employed in about 2.2 to 5 times the molar amount of the carbon disulfide, the reaction with carbon disulfide is effected at a temperature of about 30° C. to 45° C. and the heating is effected at a temperature between about 60° C. and 80° C., excess hydrazine being recycled in the mother liquor.

7. The process of claim 6, wherein the carbon disulfide is introduced into the solution as fine jets of liquid which, because of their large surface area, react rapidly with the solution before rising to the surface of the solution.

8. A process of claim 4, wherein a part of the mother liquor which is not recycled is treated to recover thiocarbohydrazide contained therein.

9. In a process for the production of thiocarbohydrazide by the thermal treatment of hydraziniumdithiocarbazinate in hydrazine hydrate as the reaction medium, the improvement which comprises carrying out said thermal treatment at a temperature of 50° C. to 90° C. in aqueous hydrazine hydrate in which hydrogen sulfide is present in amount to obtain thiocarbohydrazide in a yield of at least 80%.

10. A process as claimed in claim 9 wherein said thermal treatment is carried out at a temperature of about 60° C. to 85° C.

11. A process as claimed in claim 9 wherein said thermal treatment is carried out at a temperature of about 69° C. to 75° C.

* * * * *